United States Patent [19]

Barberet et al.

[11] Patent Number: Plant 6,276

[45] Date of Patent: Sep. 6, 1988

[54] CARNATION VARIETY "LONCITRA"

[75] Inventors: Nicole Barberet; Yves Ducloux, both of Antibes, France

[73] Assignee: Laboratoire de Physiologie Vegetale de la Londe, La Londe, France

[21] Appl. No.: 889,905

[22] Filed: Jul. 28, 1986

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new variety of standard carnation particularly distinguished by its medium sized flowers of light red or Rose Bengal overall coloration which are borne singly on long, strong stems; the plant having a tall, vigorous and upright growth habit blooming recurrently in spring, midseason and fall with a tendency to give fewer blooms in fall.

1 Drawing Sheet

BACKGROUND OF THE NEW PLANT

Our new standard carnation cultivar originated as a sport or natural mutation of the variety 'Lonsico' (U.S. Plant Pat. No. 5,446) being grown at La Londe, Les Maures, France. This plant was discovered by us at La Londe in 1981, and selected for propagation and test because of the very light red coloration of its medium sized blooms which were borne on long, strong stems on a tall plant having moderately abundant foliage and a vigorous and rather rigid growth habit with an abundant production of blooms. This sport was asexually reproduced by cuttings with very satisfactory results and subsequently we directed that this new plant be propagated through several successive generations by cuttings, which demonstrated clearly that the novel characteristics of our discovery would hold true from generation to generation and were firmly fixed.

DESCRIPTION OF THE DRAWING

Our new variety of carnation plant is illustrated by the accompanying photographic drawing which shows, in full color, a group of flowering stems including buds and blooms in various stages of opening, the colors shown being as nearly true to those specified herein as is reasonably possible to obtain by conventional photographic procedures.

DESCRIPTION OF THE NEW PLANT

The following is a detailed description of our new carnation variety based upon observations of greenhouse grown plants at La Londe, Les Maures, France, and at Antibes, France, early in 1986, the color designations being specified according to The R.H.S. Colour Chart published by The Royal Horticultural Society of London, England.

THE PLANT

Origin: Sport.

Parentage: Variety 'Lonsico' (U.S. Plant Pat. No. 5,446).

Classification:

*Botanic.*—*Dianthus caryphyllus.*

*Commercial.*—Standard carnation.

Form: Tall, erect bush having at least four stems emitted near the ground from the main stem.

Height: Averages about 94 cm. at eight months.

Main stem length: Less than 15 cm. due to pinching.

Branching character: Only a few branches.

Growth habit: Vigorous, upright and rather rigid.

Foliage:

*Quantity.*—Moderately abundant.

*Number of leaves.*—More than 120.

*Leaf size.*—Averages about 15.8 cm. long and about 1.1 cm. wide at the seventh node.

*Shape.*—Linear with curved margins and acuminate apex.

*Texture.*—Leathery.

*Color.*—Upper side — 189A. Under side — 189A.

*Ribs, veins and Rachis.*—Hardly noticeable.

THE BUD

Form: Ovoid.

Size: Medium.

*Diameter.*—Averages about 2.2 cm.

*Length.*—Averages about 3 cm.

Color of petals:

*When sepals first divide.*—57D.

*When petals begin to unfurl.*—57C.

Sepals:

*Number.*—Five.

*Shape.*—The sepals are joined at the bottom and the upper portion is acute with mucronate tips. The sepals are hooded over the bud before dividing and stand up when the flower opens.

*Color.*—Inside — 149D. Outside — 145A and 143C.

*Striae.*—Longitudinal.

Calyx:

*Size.*—Medium.

*Shape.*—Columnar.

*Splitting.*—The calyx rarely splits.

*Aspect.*—Smooth.

Flower stem:

*Length.*—Averages about 70 cm.

*Character.*—Erect and rather rigid.

*Color.*—189A.

THE FLOWER

Blooming habit: Recurrent and profusely in spring, midseason and fall with a tendency to give fewer blooms in fall.

Size: Medium.

*Diameter.*—Averages about 8 cm.
*Depth.*—Averages about 5 cm.
Borne: Singly on strong, upright stems.
Shape:
*When bloom first opens.*—High centered.
*When bloom matures.*—Ball shaped.
Petalage:
*Number of petals.*—Averages about 58.
*Arrangement.*—Imbricated.
*Form.*—Semi-circular with finely serrated outer end margins.
*Texture.*—Soft.
*Appearance.*—Satiny.
*Color.*—Outer petals: Body — 57C with whitish base. Reverse side — 57D. Inner petals: Body — 57C. Base — Whitish. Reverse side — 57D.
Petaloids:
*Number.*—Less than ten.
*Size.*—Smaller than the petals.
*Color.*—The same as the petals.
Flower stem:
*Length.*—Averages 70 cm. when cut at the tenth node.
*Color.*—189A.
*Character.*—Upright with good strength.
Persistence: The petals hang on and dry.
Fragrance: Strong.
Disease resistance: Rather tolerant to *Fusarium oxysporum* as observed I.N.R.A. Antibes, France.

Lasting quality:
*As a cut flower.*—At least ten days in vase keeping.

REPRODUCTIVE ORGANS

Stamens:
*Number.*—3 to 10.
*Arrangement.*—Around the ovary.
*Anthers.*—Size: About 4 mm. Color: Greenish white.
*Filaments.*—Length: Averages about 2 cm. Color: White.
Pistils:
*Number.*—Two.
*Styles.*—Length: Averages about 1.9 cm. Color: White.
*Stigmas.*—Color: Whitish.
Character of ovary: The ovary is ribbed.

When compared with the parent 'Lonsico', this mutation has a much lighter coloration. Otherwise the new plant has about the same characteristics as the parent.

We claim:

1. A new and distinctive carnation cultivar of the standard type, substantially as herein shown and described, characterized by the light red overall coloring of its medium sized blooms which are borne on long, strong stems having moderately abundant foliage, the plant blooming recurrently and profusely during the growing season.

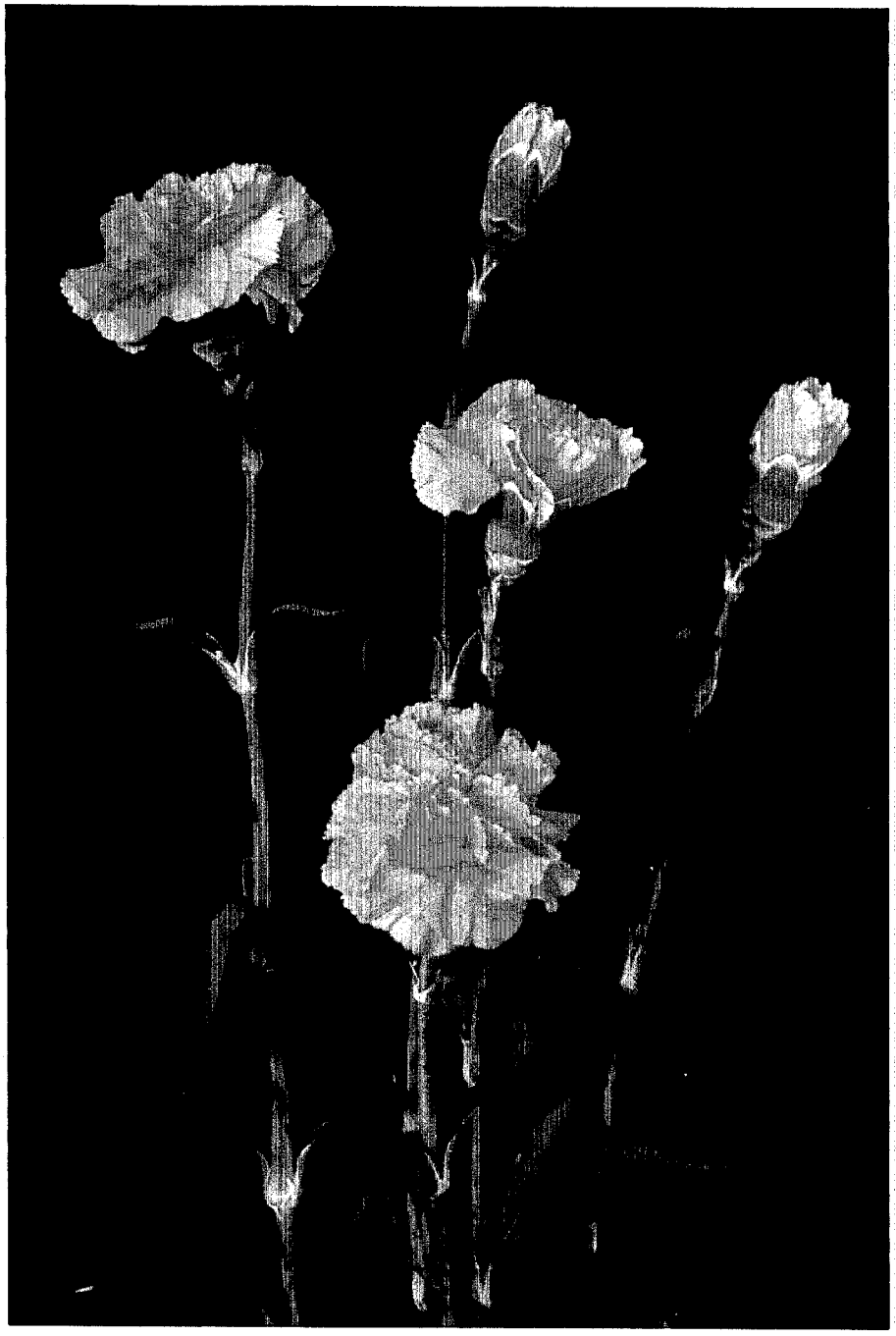

* * * * *